(12) United States Patent
Sana et al.

(10) Patent No.: US 7,504,213 B2
(45) Date of Patent: Mar. 17, 2009

(54) METHODS AND APPARATUS FOR PREPARING ARRAYS COMPRISING FEATURES HAVING DEGENERATE BIOPOLYMERS

(75) Inventors: Theodore R. Sana, San Mateo, CA (US); Eric M. Leproust, San Jose, CA (US); Paul K. Wolber, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 426 days.

(21) Appl. No.: 10/722,155

(22) Filed: Nov. 25, 2003

(65) Prior Publication Data

US 2005/0019786 A1 Jan. 27, 2005

Related U.S. Application Data

(60) Continuation-in-part of application No. 10/266,474, filed on Oct. 7, 2002, which is a division of application No. 09/350,969, filed on Jul. 9, 1999, now Pat. No. 6,461,816.

(51) Int. Cl.
*C12Q 1/68* (2006.01)
*C12P 19/34* (2006.01)
*C07H 21/02* (2006.01)

(52) U.S. Cl. .............................. 435/6; 435/6; 435/91.1; 435/91.2

(58) Field of Classification Search ........................ None
See application file for complete search history.

(56) References Cited

U.S. PATENT DOCUMENTS

| | | | |
|---|---|---|---|
| 6,027,880 A * | 2/2000 | Cronin et al. ................... | 435/6 |
| 6,103,463 A * | 8/2000 | Chetverin et al. .............. | 435/6 |
| 6,180,351 B1 | 1/2001 | Cattell | |
| 6,232,072 B1 | 5/2001 | Fisher | |
| 6,242,266 B1 | 6/2001 | Schleifer et al. | |
| 6,251,588 B1 | 6/2001 | Shannon et al. | |
| 6,251,595 B1 | 6/2001 | Gordon et al. | |
| 6,306,599 B1 | 10/2001 | Perbost | |
| 6,323,043 B1 | 11/2001 | Caren et al. | |
| 6,372,483 B2 | 4/2002 | Schleifer et al. | |
| 6,461,816 B1 | 10/2002 | Wolber et al. | |
| 6,589,739 B2 | 7/2003 | Fisher | |
| 6,599,693 B1 | 7/2003 | Webb | |
| 6,613,893 B1 | 9/2003 | Webb | |
| 2003/0112295 A1 | 6/2003 | DaQuino et al. | |
| 2003/0124588 A1 | 7/2003 | Wolber et al. | |
| 2003/0143329 A1 | 7/2003 | Shchegrova et al. | |
| 2003/0143756 A1 | 7/2003 | Fisher et al. | |
| 2004/0002072 A1 | 1/2004 | Barth et al. | |
| 2004/0005614 A1 | 1/2004 | Kurn et al. | |
| 2004/0009608 A1 | 1/2004 | Caren et al. | |

FOREIGN PATENT DOCUMENTS

| | | |
|---|---|---|
| WO | WO 9525116 A1 * | 9/1995 |
| WO | WO 9922025 A1 * | 5/1999 |
| WO | WO 00/40758 | 7/2000 |

OTHER PUBLICATIONS

Hanks et al., "Use of Degenerate Oligonucleotide Probes to Identify Clones that Encode Protein Kinases," Methods in Enzymology, 1991, vol. 200, pp. 525-532.*
Kafatos et al., Nucleic Acids Research.(1979) 7(6): 1541-1552; Determination of Nucleic Acid Sequence Homologies and Relative Concentrations by a Dot Hybridization Procedure.
Chee, et al., Science. (1996) 274:610-614; Accessing Genetic Information with High-Density DNA Arrays.
Wodicka, et al., Nature Biotechnology. (1997) 15:1359-1367; Genome-wide Expression Monitoring in *Saccharomyses cerevisiae*.

* cited by examiner

*Primary Examiner*—Young J Kim

(57) ABSTRACT

Methods and apparatus are disclosed for synthesizing a plurality of biopolymers at predetermined feature locations on a surface of a substrate. One or more of the feature locations comprises degenerate biopolymers. One or more biopolymer subunit precursors are added, in multiple rounds of subunit additions, at each of multiple feature locations on the surface to form the plurality of biopolymers on the surface. For each feature location comprising degenerate biopolymers, the biopolymer subunit precursors comprise a mixture of biopolymer subunit precursors for forming the degenerate biopolymers at the feature location.

28 Claims, 4 Drawing Sheets

METHODS AND APPARATUS FOR PREPARING ARRAYS COMPRISING FEATURES HAVING DEGENERATE BIOPOLYMERS

CROSS-REFERENCE TO RELATED APPLICATIONS

This application is a continuation-in-part of U.S. patent application Ser. No. 10/266,474 filed Oct. 7, 2002, which is a divisional of U.S. patent application Ser. No. 09/350,969, filed on Jul. 9, 1999 now U.S. Pat. No. 6,461,816, the disclosures of which are incorporated herein by reference.

BACKGROUND OF THE INVENTION

Molecular methods using DNA probes, nucleic acid hybridizations and in vitro amplification techniques are promising methods offering advantages to conventional methods used for patient diagnoses, biomedical research or basic biology research. Recent advances in such methods often include the introduction of parallelism, i.e., performing many experiments with the same effort previously used to perform a single experiment. However, the introduction of parallelism often forces changes in the methods used to design such experiments.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactively, chemically and fluorescently labeled nucleoside triphosphates of high specific activity have made it possible to identify, isolate, and characterize various nucleic acid sequences of biological interest. Nucleic acid hybridization has great potential in diagnosing or characterizing diseased or altered tissue function associated with unique nucleic acid sequences or gene expression states. Unique nucleic acid sequences may result from genetic or environmental change in DNA by insertions, deletions, point mutations, or by acquiring foreign DNA or RNA by means of infection by bacteria, molds, fungi, and viruses. Altered gene expression states may arise from neoplastic transformation, viral infection, environmental insult or drug treatment. It is desirable to perform such experiments in parallel; earlier methods for introducing modest parallelism include Southern blots, Northern blots and slot blots.

Such blot techniques are examples of methods for detecting nucleic acids that employ nucleic acid probes that have sequences complementary to sequences in the target nucleic acid. A nucleic acid probe may be, or may be capable of being, labeled with a reporter group or may be, or may be capable of becoming, bound to a support. Detection of signal depends upon the nature of the label or reporter group. Usually, the probe is comprised of natural nucleotides such as ribonucleotides and deoxyribonucleotides and their derivatives although unnatural nucleotide mimetics such as peptide nucleic acids and oligomeric nucleoside phosphonates are also used. Commonly, binding of the probes to the target is detected by means of a label incorporated into the probe. Alternatively, the probe may be unlabeled and the target nucleic acid labeled. Binding can be detected by separating the bound probe or target from the free probe or target and detecting the label. In one approach, a sandwich is formed comprised of one probe, which may be labeled, the target and a probe that is or can become bound to a surface. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target, allowing the target to hybridize to a surface-bound probe, washing away the unbound target and detecting the labeled target that remains.

Direct detection of labeled target hybridized to surface-bound probes is particularly advantageous if the surface contains a mosaic of different probes that are individually localized to discrete, known areas of the surface. Such ordered arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. One difficulty in the design of oligonucleotide arrays is that oligonucleotides targeted to different regions of the same gene can show large differences in hybridization efficiency, presumably due to the interplay between the secondary structures of the oligonucleotides and their targets and the stability of the final probe/target hybridization product.

Recently, a method or algorithm was described for predicting oligonucleotides specific for a target nucleic acid where the oligonucleotides exhibit a high potential for hybridization (Shannon, et al., Method for evaluating oligonucleotide probe sequences, U.S. Pat. No. 6,251,588 (2001)). The algorithm uses parameters of the oligonucleotide and the oligonucleotide:target nucleotide sequence duplex, which can be readily predicted from the primary sequences of the target polynucleotide and candidate oligonucleotides. In the method, oligonucleotides are filtered based on one or more of these parameters, then further filtered based on the sizes of clusters of oligonucleotides. The basic steps involved in the disclosed method involve parsing a sequence that is complementary to a target nucleotide sequence into a set of overlapping oligonucleotide sequences, calculating one or more parameters for each of the oligonucleotide sequences with respect to its hybridization to the target nucleotide sequence, filtering the oligonucleotide sequences based on the values for each parameter, filtering the oligonucleotide sequences based on the length of contiguous sequence elements and ranking the contiguous sequence elements based on their length. Certain oligonucleotides within the longest contiguous sequence elements generally showed the highest hybridization efficiencies.

In many assays there may be one or more target or non-target nucleic acids present that have nucleotide sequences that are closely related to one another differing by only a few, e.g., one to five nucleotides, at one or more sites within the nucleotide sequence. One such instance of related sequences is a family of genes that are phylogenetically related and that share stretches of conserved and/or hypervariable domains.

Recently, methods, reagents and kits were disclosed for selecting target-specific oligonucleotide probes, which may be used in analyzing a target nucleic acid sequence (see, for example, U.S. Pat. No. 6,461,816 B1 and Agilent Technologies Inc. (Palo Alto, Calif.) brochure dated Nov. 1, 2001, entitled "Development of an in situ synthesized oligonucleotide microarray for gene expression monitoring of the budding yeast Saccharomyces cerevisiae," by Stephanie Fulmer-Smentek, et al.). In the method a cross-hybridization oligonucleotide probe is identified based on a candidate target-specific oligonucleotide probe for the target nucleic acid sequence. The cross-hybridization oligonucleotide probe measures the extent of occurrence of a cross-hybridization event having a predetermined probability. Cross-hybridization results are determined employing the cross-hybridization oligonucleotide probe and the target-specific oligonucleotide probe. The target-specific oligonucleotide probe is selected or rejected for the set based on the cross-hybridization results. The process for identifying and selecting the minimum number of cross-hybridization oligonucleotide probes may be carried out using different approaches such as mismatch probe design by homology, mismatch probes that incorporate base combinations, mismatch probes that delete bases, mismatch probes that insert bases, and combinations thereof.

There remains, however, a need to prepare arrays that efficiently and effectively detect and estimate subgroups of gene families by the relative abundance of nucleic acid sequences among pools of phylogenetically related sequences that share stretches of conserved and/or hypervariable domains. Ideally, the methods should be able to employ current manufacturing techniques for the preparation of arrays with some or no modifications except to the extent of carrying out the present methods.

SUMMARY OF THE INVENTION

One embodiment of the present invention is a method for synthesizing a plurality of biopolymers at predetermined feature locations on a surface of a substrate. One or more of the feature locations comprises degenerate biopolymers. One or more biopolymer subunit precursors are added, in each round of multiple rounds of subunit additions, at each of multiple feature locations on the surface to form the plurality of biopolymers on the surface. For one or more feature locations comprising degenerate biopolymers, the biopolymer subunit precursors comprise a mixture of biopolymer subunit precursors for forming the degenerate biopolymers at the feature location.

Another embodiment of the present invention is an addressable array prepared by the above methods. The array comprises a substrate having a surface and a plurality of features on the surface wherein the features comprise biopolymers and wherein at least one of the features comprises degenerate biopolymers. The above addressable array may be employed in a method for detecting a target nucleic acid sequence. A medium suspected of containing the target nucleic acid sequence is contacted with the above array and a result of the contacting, the result indicating the presence or absence of the target nucleic acid sequence in the medium.

Another embodiment of the present invention is an addressable array prepared by the above method. The array comprises a substrate having a surface and a plurality of sites on the surface wherein the sites comprise oligonucleotides and wherein at least one of the sites comprises a polymorphically related oligonucleotide. Another embodiment of the present invention is a method for detecting a target nucleic acid sequence. A medium suspected of containing the target nucleic acid sequence is contacted with the above array. The result of the contacting is determined where the result indicates the presence or absence of the target nucleic acid sequence in the medium.

Another embodiment of the present invention is an apparatus for synthesizing an array of biopolymers on a surface of a substrate. The apparatus comprises a dispensing device comprising a plurality of nozzle groups. Each of the nozzle groups is in fluid communication with a reservoir wherein at least one of the reservoirs contains a mixture of biopolymer subunit precursors.

Another embodiment of the present invention is an apparatus for synthesizing an array of biopolymers on a surface of a substrate. The apparatus comprises a dispensing device comprising a plurality of nozzle groups. Each of the nozzle groups is in fluid communication with a reservoir. Each of the reservoirs contains a fluid comprising a single biopolymer subunit precursor. The apparatus further comprises a control unit that activates the dispensing device to dispense one or more drops of fluid comprising the biopolymer subunit precursor at individual feature sites on the surface to deposit a single biopolymer subunit precursor at an individual feature site or to deposit two or more biopolymer subunit precursors at an individual feature site to form a mixture of biopolymer subunit precursors at the individual feature site.

Another embodiment of the present invention is a method for normalizing results of binding reactions involving a plurality of samples suspected of containing target molecules and a plurality of arrays where each array comprises features on a surface of a substrate. A respective array from the plurality of arrays is contacted with a respective sample from the plurality of samples under conditions for binding to occur between target molecules in the sample and biopolymers on the surface. Each of the arrays comprises a plurality of biopolymers at predetermined feature locations on the surface. One or more of the feature locations on each of the arrays comprise molecules of the same degenerate biopolymers. The arrays are examined for the results of the binding reactions. The results of the binding reactions involving the degenerate biopolymers are used to normalize the results of the binding reactions.

BRIEF DESCRIPTION OF THE DRAWINGS

The following figures are included to better illustrate the embodiments of the apparatus and technique of the present invention. The figures are not to scale and some features may be exaggerated for the purpose of illustrating certain aspects or embodiments of the present invention.

DETAILED DESCRIPTION OF SPECIFIC EMBODIMENTS

Figure 1:
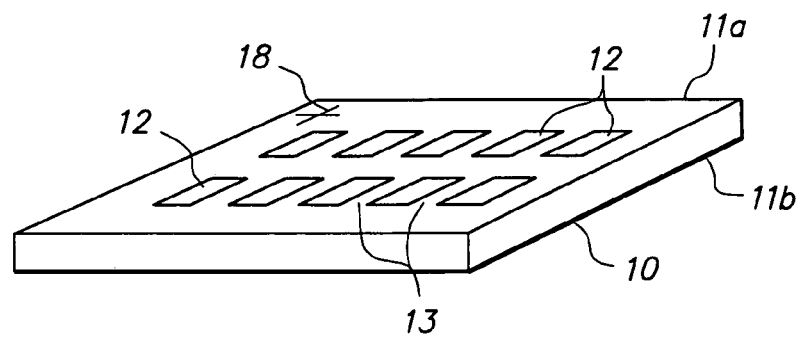
FIG. 1 is a perspective view of a substrate bearing multiple arrays, as may be produced by a method and apparatus of the present invention.

Embodiments of the present invention utilize droplet dispensing devices commonly used in array manufacture to prepare arrays of features, which normally comprise a biopolymer. In the present invention, at least one of the features comprises a group of biopolymers representing a set of related sequences. The sequences are related because they comprise one or more sites of degeneracy, e.g., the sequences are phylogenetically related or polymorphically related. The droplet dispensing devices comprise a plurality of nozzles for dispensing biopolymer subunit precursors to a surface of a substrate on which the array of features is synthesized. Each nozzle of the droplet dispensing device is normally in fluid communication with a source of a polymer unit. In one approach at least one feature is prepared by dispensing biopolymer subunit precursors to the feature site using a separate nozzle or group of nozzles for each biopolymer subunit precursor followed by exposing the site to activator and repeating the cycle of adding biopolymer subunits to the growing chain of biopolymer subunits. In another approach at least one feature is prepared by dispensing the biopolymer subunit precursors to the feature site as a mixture of biopolymer subunit precursors where activator may be present before or after the dispensing of the biopolymer subunit precursors in any one round of synthesis of the biopolymer chain.

Embodiments of the present invention enable the synthesis of a heterogeneous or complex population of oligonucleotides sequences in any single feature that share a stretch or stretches of nucleotide monomer precursor degeneracy. The methods of embodiments of the invention permit the creation of arrays with a subset of features that contain probes with maximum universality to a pool of complementary target(s).

An embodiment of the present invention is a method for synthesizing a plurality of biopolymers at predetermined feature locations on a surface of a substrate wherein one or more of the feature locations comprise degenerate biopolymers. One or more biopolymer subunit precursors are added, in each round of multiple rounds of subunit additions, at each of multiple feature locations on the surface to form the plurality of biopolymers on the surface. For one or more feature locations comprising degenerate biopolymers, the biopolymer subunit precursors comprise a mixture of biopolymer subunit precursors for forming the degenerate biopolymers at the feature location. Each round of subunit additions comprises dispensing from a dispensing system the biopolymer subunit precursors to the discrete sites, dispensing activator to the discrete sites, and (c) repeating the above steps.

Another embodiment of the present invention is a method for synthesizing a plurality of oligonucleotides at predetermined sites on a surface of a substrate. One or more of the sites comprises a mixture of oligonucleotides that are polymorphically related. One or more nucleotide precursors are added, in each round of multiple rounds of subunit additions, at each of multiple sites on the surface to form the plurality of oligonucleotides on the surface. For one or more sites comprising a mixture of polymorphically related oligonucleotides, the nucleotides comprise a mixture of nucleotides for forming the polymorphically related oligonucleotides at the site. Each round of subunit additions comprises dispensing from a dispensing system the nucleotides to the discrete sites, dispensing activator to the discrete sites, and repeating the above steps until the plurality of oligonucleotides are synthesized.

Arrays synthesized in accordance with embodiments of the present invention can be used in a number of different ways. For example, such arrays can serve as a positive control for prokaryotes, eukaryotes or samples containing mixtures and, therefore, can be compared across all arrays.

Terminology

Before proceeding further with a description of specific embodiments of the present invention, a number of terms will be defined.

The term "biomonomer" references a single unit, which can be linked with the same or other biomonomers to form a biopolymer (for example, a single amino acid or nucleotide with two linking groups one or both of which may have removable protecting groups). A reagent fluid or biomonomer fluid or biopolymer fluid refers to a liquid containing either a biomonomer or biopolymer, respectively (typically in solution).

The term "biopolymer" refers to a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions.

The phrase "degenerate biopolymers" refers to biopolymers that comprise one or more sites of degeneracy, for example, less than 10, less than 5, less than 3, or less 2 such sites. A site of degeneracy generally comprises a contiguous stretch of 1 to 5 nucleotides in length, one to 4 nucleotides in length, one to 3 nucleotides in length, one to 2 nucleotides in length, one nucleotide in length. The nucleotides of the degenerate sites are degenerate nucleotides where the nucleotide(s) of a respective degenerate site differ from nucleotide(s) in corresponding positions of another biopolymer, the biopolymers being otherwise generally of the same sequence composition. The nature and number of nucleotides in a degenerate site are generally determined by the nature of related sequences in a target sample whether the composition of such target sample is known or unknown.

The term "polynucleotide" or "nucleic acid" refers to a compound or composition that is a polymeric nucleotide or nucleic acid polymer. The polynucleotide may be a natural compound or a synthetic compound. The polynucleotide can have from about 2 to 5,000,000 or more nucleotides. The larger polynucleotides are generally found in the natural state. In an isolated state the polynucleotide can have about 10 to 50,000 or more nucleotides, usually about 100 to 20,000 nucleotides. It is thus obvious that isolation of a polynucleotide from the natural state often results in fragmentation. It may be useful to fragment longer target nucleic acid sequences, particularly RNA, prior to hybridization to reduce competing intramolecular structures.

The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, cosmids, the genomes of biological material such as microorganisms, e.g., bacteria, yeasts, phage, chromosomes, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site-specific chemical cleavage method.

The nucleic acids may be generated by in vitro replication and/or amplification methods such as the Polymerase Chain Reaction (PCR), asymmetric PCR, the Ligase Chain Reaction (LCR), transcriptional amplification by an RNA polymerase, and so forth. The nucleic acids may be either single-stranded or double-stranded. Single-stranded nucleic acids are preferred because they lack complementary strands that compete for the oligonucleotide probes during the hybridization step of the method of the invention. A nucleic acid may be treated to render it denatured or single stranded by treatments that are well known in the art and include, for instance, heat or alkali treatment, or enzymatic digestion of one strand.

The phrase "related nucleic acid sequences" refers to two or more nucleic acid sequences that contain regions of nucleotides that are the same among the related sequences and diverge with one or more intervening sequences. The sequences may be related by identity, i.e., the number of contiguous nucleotides that are the same, by functionality, and so forth. For example, one may assign a BLAST® score based on a particular evolutionary matrix such as BLOSSUM®. In this way sequences with as low as 25% identity (over the entire sequence) that are members of the same functional gene family are still related. One instance of related nucleic acid sequences is phylogenetically related sequences that share stretches of conserved and/or hypervariable domains. The "related nucleic acid sequences" may have variations in nucleotides such as in a "mutation," for example, single nucleotide polymorphisms. In general, the variations occur from individual to individual. The mutation may be a change in the sequence of nucleotides of normally conserved nucleic acid sequence resulting in the formation of a mutant as differentiated from the normal (unaltered) or wild-type sequence. Point mutations (i.e. mutations at a single base position) can be divided into two general classes, namely, base-pair substitutions and frameshift mutations. The latter entail the insertion or deletion of a nucleotide pair. Mutations that insert or delete multiple base pairs are also possible; these can leave the translation frame unshifted, permanently shifted, or shifted over a short stretch of sequence. A difference of a single nucleotide can be significant so as to change the phenotype.

The phrase "target nucleotide sequence" or "target nucleic acid sequence" or "target polynucleotide" refers to a sequence of nucleotides to be identified, detected or otherwise analyzed, usually existing within a portion or all of a polynucleotide. In the present invention the identity of the target nucleotide sequence may be known to an extent sufficient to allow preparation of various sequences hybridizable with the target nucleotide sequence and of oligonucleotides, such as probes and primers, and other molecules necessary for conducting methods in accordance with the present invention, related methods and so forth. In any particular assay involving arrays, the number of target nucleotide sequences may be one to nine, or tens, hundreds, thousands, and so forth.

The target sequence usually contains from about 10 to 5,000 or more nucleotides, preferably 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of identification, detection, amplification, and/or other analysis of the target nucleotide sequence, where appropriate.

It is to be noted that the usage of the terms "probe" and "target" in the literature may vary. For example, when describing non-homogeneous diagnostic assays, the term "probe" may be used to refer to an immobilized or surface-bound species, and the term target may be used to refer to a species in solution (the "target" of the assay). Such usage of the terms is the opposite of the usage sometimes seen in the molecular biology literature. The present application uses the diagnostic assay definitions of the terms "probe" and "target" as discussed herein.

The term "oligonucleotide" refers to a polynucleotide, usually single stranded, either a synthetic polynucleotide or a naturally occurring polynucleotide. The length of an oligonucleotide is generally governed by the particular role thereof, such as, for example, probe, primer, predictor and the like. Various techniques can be employed for preparing an oligonucleotide. Such oligonucleotides can be obtained by biological synthesis or by chemical synthesis. For short oligonucleotides (up to about 100 nucleotides), chemical synthesis will frequently be more economical as compared to biological synthesis. In addition to economy, chemical synthesis provides a convenient way of incorporating low molecular weight compounds and/or modified bases during specific synthesis steps. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. Methods of oligonucleotide synthesis include phosphotriester and phosphodiester methods (Narang, ET al. (1979) Meth. Enzymol 68:90) and synthesis on a support (Beaucage, et al. (1981) Tetrahedron Letters 22:1859-1862) as well as phosphoramidite techniques (Caruthers, M. H., et al., "Methods in Enzymology," Vol. 154, pp. 287-314 (1988)) and others described in "Synthesis and Applications of DNA and RNA," S. A. Narang, editor, Academic Press, New York, 1987, and the references contained therein.

Oligonucleotides may be employed, for example, as oligonucleotide probes or primers. The term "oligonucleotide probe" refers to an oligonucleotide employed to bind to a portion of a polynucleotide such as another oligonucleotide or a target nucleotide sequence. The design, including the length, and the preparation of the oligonucleotide probes are generally dependent upon the sequence to which they bind and their function in the methods of the invention.

The phrase "nucleoside triphosphates" refers to nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP. The term "nucleoside triphosphates" also includes derivatives and analogs thereof, which are exemplified by those derivatives that are recognized and polymerized in a similar manner to the underivatized nucleoside triphosphates.

The term "nucleotide" or "nucleotide base" or "base" refers to a base-sugar-phosphate combination that is the monomeric unit of nucleic acid polymers, i.e., DNA and RNA. The term as used herein includes modified nucleotides. In general, the term refers to any compound containing a cyclic furanoside-type sugar (β-D-ribose in RNA and β-D-2'-deoxyribose in DNA), which is phosphorylated at the 5' position and has either a purine or pyrimidine-type base attached at the C-1' sugar position via a β-glycosol C1'-N linkage. The nucleotide may be natural or synthetic.

The phrase "biopolymer subunit precursor" refers to a reactive biopolymer subunit that can add to a growing chain of biopolymer subunits. The reactive biopolymer subunit comprises one or more sites of activation depending on the nature of the biopolymer subunit and the synthetic route utilized to prepare the biopolymer. The phrase "nucleotide precursor" refers to a reactive unit that can add to a growing chain of nucleotides. For example, the nucleotide precursor may be a phosphoramidite nucleotide reagent or the like.

The term "DNA" refers to deoxyribonucleic acid.

The term "RNA" refers to ribonucleic acid.

The term "nucleoside" refers to a base-sugar combination or a nucleotide lacking a phosphate moiety.

The terms "hybridization (hybridizing)" and "binding" in the context of nucleotide sequences are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like.

The term "complementary," "complement," or "complementary nucleic acid sequence" refers to the nucleic acid strand that is related to the base sequence in another nucleic acid strand by the Watson-Crick base-pairing rules. In general, two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G/U or U/G basepairs.

The term "hybrid" refers to a double-stranded nucleic acid molecule formed by hydrogen bonding between complementary nucleotides. The term "hybridize" refers to the process by which single strands of nucleic acid sequences form double-helical segments through hydrogen bonding between complementary nucleotides.

The term "stringent hybridization conditions" as used herein refers to conditions that are that are compatible to produce duplexes on an array surface between complementary binding members, for example, between probes and complementary targets in a sample, e.g., duplexes of nucleic acid probes, such as DNA probes, and their corresponding nucleic acid targets that are present in the sample, e.g., their corresponding mRNA analytes present in the sample. An example of stringent hybridization conditions is hybridization at 60° C. or higher and 3×SSC (450 mM sodium chloride/ 45 mM sodium citrate). Another example of stringent hybridization conditions is incubation at 42° C. in a solution containing 30% formamide, 1M NaCl, 0.5% sodium sarcosine, 50 mM MES, pH 6.5. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The term "substrate" or "support" refers to a porous or non-porous water insoluble material, on a surface of which one or more arrays are present. Typically, the substrate material is transparent. By "transparent" is meant that the substrate material permits signal from features on the surface of the substrate to pass therethrough without substantial attenuation and also permits any interrogating radiation to pass therethrough without substantial attenuation. By "without substantial attenuation" may include, for example, without a loss of more than 40% or more preferably without a loss of more than 30%, 20% or 10%, of signal. The interrogating radiation and signal may for example be visible, ultraviolet or infrared light. In certain embodiments, such as for example where production of binding pair arrays for use in research and related applications is desired, the materials from which the substrate may be fabricated should ideally exhibit a low level of non-specific binding during hybridization events.

The materials for the substrate may be naturally occurring or synthetic or modified naturally occurring. Suitable rigid substrates may include glass, which term is used to include silica, and include, for example, glass such as glass available as Bioglass, and suitable plastics. Should a front array location be used, additional rigid, non-transparent materials may be considered, such as silicon, mirrored surfaces, laminates, ceramics, opaque plastics, such as, for example, polymers such as, e.g., poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc., either used by themselves or in conjunction with other materials. The surface of the substrate is usually the outer portion of a substrate.

The surface of the material onto which the biopolymers are formed may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethylene amines, polyarylene sulfides, polysiloxanes, polyimides, polyacetates, and the like, where the polymers may be hetero- or homo-polymeric, and may or may not have separate functional moieties attached thereto (for example, conjugated). Various further modifications to the particular embodiments described above are, of course, possible. Accordingly, the present invention is not limited to the particular embodiments described in detail above.

The material used for an array support or substrate may take any of a variety of configurations ranging from simple to complex. Usually, the material is relatively planar such as, for example, a slide. In many embodiments, the material is shaped generally as a rectangular solid. As mentioned above, multiple arrays of chemical compounds may be synthesized on a sheet, which is then diced, i.e., cut by breaking along score lines, into single array substrates. Typically, the substrate has a length in the range about 5 mm to 100 cm, usually about 10 mm to 25 cm, more usually about 10 mm to 15 cm, and a width in the range about 4 mm to 25 cm, usually about 4 mm to 10 cm and more usually about 5 mm to 5 cm. The substrate may have a thickness of less than 1 cm, or even less than 5 mm, 2 mm, 1 mm, or in some embodiments even less than 0.5 mm or 0.2 mm. The thickness of the substrate is about 0.01 mm to 5.0 mm, usually from about 0.1 mm to 2 mm and more usually from about 0.2 to 1 mm. The substrate is usually cut into individual test pieces, which may be the size of a standard size microscope slide, usually about 3 inches in length and 1 inch in width.

Binding of oligonucleotides to a surface of a substrate may be accomplished by well-known techniques, commonly available in the literature. See, for example, A. C. Pease, et al., *Proc. Nat. Acad. Sci. USA,* 91:5022-5026 (1994).

The phrase "amplification of nucleic acids or polynucleotides" refers to any method that results in the formation of one or more copies of a nucleic acid or polynucleotide molecule (exponential amplification) or in the formation of one or more copies of only the complement of a nucleic acid or polynucleotide molecule (linear amplification).

The term "drop" or "droplet" refers to a small amount of liquid traveling in a space, and while often approximately spherical if no external forces are acting upon it, may have other shapes depending upon those other forces. A drop that has contacted a substrate is often referred to as a deposited drop, although sometimes it will be simply referenced as a drop when it is understood that it was previously deposited.

The phrase "droplet dispensing device" includes any device that dispenses drops of fluid, usually, a liquid. The droplet dispensing device normally includes a reagent source or manifold or reservoir as well as reagent lines that connect the source to fluid dispensing nozzles and the like. The "reservoir" may be any container that is suitable for containing a fluid reagent.

The phrase "pulse jet" refers to a device that can dispense drops by delivering a pulse of pressure (such as by a piezoelectric or thermoelectric element) to liquid adjacent an outlet or orifice such that a drop will be dispensed therefrom.

An "array" includes any one-, two- or three-dimensional arrangement of addressable regions bearing a particular feature such as a biopolymer, e.g., polynucleotides, associated with that region. An array is addressable in that it has multiple regions of different moieties, for example, different polynucleotide sequences, such that a region or feature or spot of the array at a particular predetermined location or address on the array can detect a particular target molecule or class of target molecules although a feature may incidentally detect non-target molecules of that feature.

An array assembly on the surface of a substrate refers to one or more arrays disposed along a surface of an individual substrate and separated by inter-array areas. Normally, the surface of the substrate opposite the surface with the arrays (opposing surface) does not carry any arrays. The arrays can be designed for testing against any type of sample, whether a trial sample, a reference sample, a combination of the foregoing, or a known mixture of components such as polynucleotides, proteins, polysaccharides and the like (in which case the arrays may be composed of features carrying unknown sequences to be evaluated). The surface of the substrate may carry at least one, two, four, or at least ten, arrays. Depending upon intended use, any or all of the arrays may be the same or different from one another and each may contain multiple spots or features of chemical compounds such as, e.g., biopolymers in the form of polynucleotides or other biopolymer. A typical array may contain more than ten, more than one hundred, more than one thousand or ten thousand features, or even more than one hundred thousand features, in an area of less than 20 $cm^2$ or even less than 10 $cm^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges.

Any of a variety of geometries of arrays on a substrate may be used. As mentioned above, an individual substrate may contain a single array or multiple arrays. Features of the array may be arranged in rectilinear rows and columns. This is particularly attractive for single arrays on a substrate. When multiple arrays are present, such arrays can be arranged, for example, in a sequence of curvilinear rows across the substrate surface (for instance, a sequence of concentric circles or semi-circles of spots), and the like. Similarly, the pattern of features may be varied from the rectilinear rows and columns of spots to include, for example, a sequence of curvilinear rows across the substrate surface (for example, a sequence of concentric circles or semi-circles of spots), and the like. The configuration of the arrays and their features may be selected according to manufacturing, handling, and use considerations.

Each feature, or element, within the molecular array is defined to be a small, regularly shaped region of the surface of the substrate. The features are arranged in a predetermined manner. Each feature of an array usually carries a predetermined biopolymer or mixtures thereof. Each feature within the molecular array may contain a different molecular species, and the molecular species within a given feature may differ from the molecular species within the remaining features of the molecular array. Some or all of the features may be of different compositions. Each array may contain multiple spots or features and each array may be separated by spaces or areas. It will also be appreciated that there need not be any space separating arrays from one another. Interarray areas and interfeature areas are usually present but are not essential. The interarray and interfeature areas do not carry any polynucleotide (or other biopolymer of a type of which the features are composed). Interarray areas and interfeature areas typically will be present where arrays are formed by the conventional in situ process by depositing for each feature at least one droplet of reagent such as from a pulse jet. It will be appreciated though, that the interarray areas and interfeature areas, when present, could be of various sizes and configurations.

Figure 2:
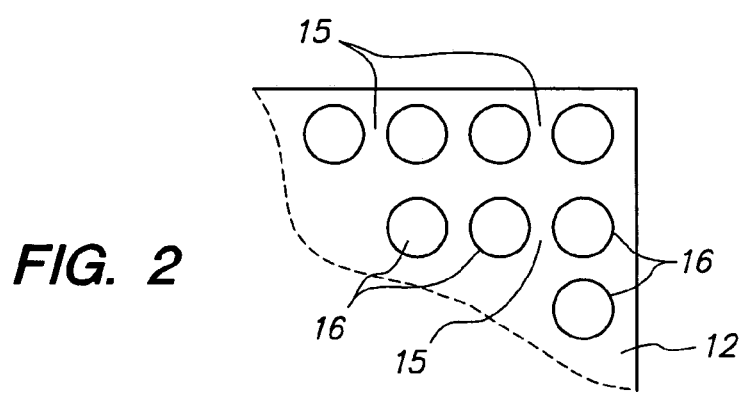
FIG. 2 is an enlarged view of a portion of FIG. 1 showing some of the identifiable individual regions (or "features") of a single array of FIG. 1.
Figure 3:
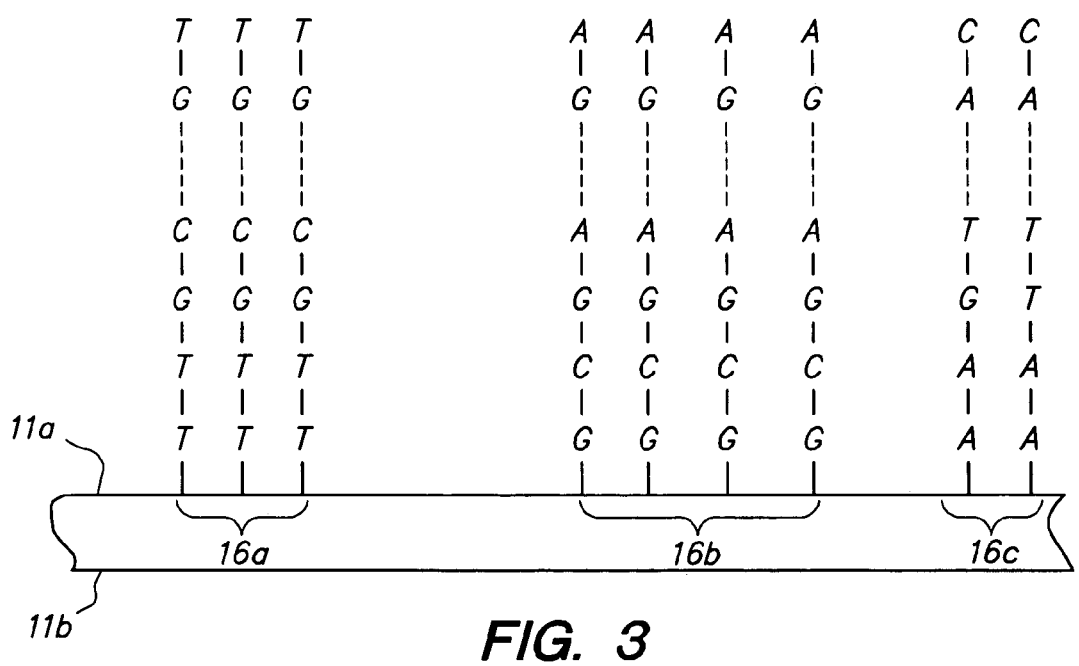
FIG. 3 is an enlarged cross-section of a portion of FIG. 2.

Referring to FIGS. 1-3, typically, embodiments of the present invention produce multiple identical arrays 12 (only some of which are shown in FIG. 1), separated by inter-array regions 13, across the complete front surface 11*a* of a single transparent substrate 10. However, the arrays 12 produced on a given substrate need not be identical and some or all could be different. Each array 12 will contain multiple spots or features 16 (16a, 16b, 16c, etc.) separated by inter-feature regions 15. A typical array 12 may contain from 100 to 100,000 features. All of the features 16 may be different, or some or all could be the same. Each feature carries a predetermined moiety (such as a particular polynucleotide sequence), or a predetermined mixture of moieties (such as a mixture of particular polynucleotides). This is illustrated schematically in FIG. 3 where different regions 16 are shown as carrying different polynucleotide sequences. As can be seen with reference to FIG. 3, feature 16c comprises two different oligonucleotides in accordance with the present invention whereas feature 16a comprises one or more copies of the same oligonucleotide and feature 16b comprises one or more copies of the same oligonucleotide, which is different from the oligonucleotide of feature 16a and those of feature 16c.

The number of features comprising more than one different oligonucleotide, i.e., degenerate biopolymers, is dependent on a number of factors including the nature of the sample if known and the like. However, embodiments of the present invention may be employed to assess samples of partially or fully unknown composition such as, for example, assessing the level of degeneracy of a particular sample. The complexity of sequences that can be synthesized in any single feature site on an array is limited by several factors including the absolute number of probes that can be synthesized per unit space, the relative coupling efficiency of nucleotide monomer precursors for attaching to the growing oligonucleotide chain and the capacity for depurination, and so forth.

The phase "hybridization efficiency" refers to the productivity of a hybridization reaction, measured as either the absolute or relative yield of oligonucleotide probe/polynucleotide target duplex formed under a given set of conditions in a given amount of time.

The phrase "homologous or substantially identical polynucleotides" refers to, in general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

The term "complementary" refers to two sequences where the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G basepairs.

The term "label" refers to a member of a signal producing system. Usually the label is part of a target nucleotide sequence or an oligonucleotide probe, either being conjugated thereto or otherwise bound thereto or associated therewith. The label is capable of being detected directly or indirectly. Labels include (i) reporter molecules that can be detected directly by virtue of generating a signal, (ii) specific binding pair members that may be detected indirectly by subsequent binding to a cognate that contains a reporter molecule, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used.

The phrase "ancillary materials" refers to various ancillary materials that may be employed in the methods and assays utilizing oligonucleotide probes in accordance with the present invention. For example, buffers and salts will normally be present in an assay medium, as well as stabilizers for the assay medium and the assay components. Frequently, in addition to these additives, proteins may be included, such as albumins, organic solvents such as formamide, quaternary ammonium salts, polycations such as spermine, surfactants, particularly non-ionic surfactants, binding enhancers, e.g., polyalkylene glycols, or the like.

The phrase "computer program" refers to a written set of instructions that symbolically instructs an appropriately configured computer to execute an algorithm that will yield desired outputs from some set of inputs. The instructions may be written in one or several standard programming languages, such as C, $C^{++}$, Visual BASIC, FORTRAN or the like. Alternatively, the instructions may be written by imposing a template onto a general-purpose numerical analysis program, such as a spreadsheet.

The phrase "adapted to" or "adapted for" is used herein with respect to components of the present apparatus. The components of the present apparatus are adapted to perform a specified function by a combination of hardware and software. This includes the structure of the particular component and may also, and usually does, include a microprocessor, embedded real-time software and I/O interface electronics to control the sequence of operations of the invention. In this way a component of an apparatus may be activated to perform a particular function.

SPECIFIC EMBODIMENTS

Embodiments of the present methods for synthesizing arrays of biopolymers utilize the known current approaches for fabrication of biopolymer arrays involving in situ synthesis methods and in some instances direct deposition techniques. The in situ synthesis methods can be basically regarded as iterating the sequence of depositing droplets of: (a) a protected monomer onto predetermined locations on the surface of a support to link with either a suitably activated surface or with a previously deposited deprotected monomer that has been or is subsequently activated with an activator so that it can now react with a subsequently deposited protected monomer; (b) deprotecting the deposited monomer; and (c) depositing another protected monomer for linking. The addition of activator may be carried out after addition of protected monomers so that deposited protected monomers do not add to the growing chain until activator is added. Different monomers may be deposited at different regions on the substrate during any one iteration so that the different regions of the completed array will have different desired biopolymer sequences. One or more intermediate steps may be required in each iteration such as, for example, capping or blocking, oxidation, deprotection of protection groups or deblocking, and washing steps. The in situ synthesis methods include those described in U.S. Pat. No. 5,449,754 for synthesizing peptide arrays, as well as WO 98/41531 and the references cited therein for synthesizing polynucleotides (specifically, DNA).

The in situ method for fabricating a polynucleotide array typically follows, at each of the multiple different addresses at which features are to be formed, the same conventional iterative sequence used in forming polynucleotides from nucleoside reagents on a substrate by means of known chemistry. This iterative sequence is as follows: (a) coupling an activated selected nucleoside (phosphoramidite monomer) through a phosphite linkage to a functionalized substrate in the first iteration, or a nucleoside bound to the substrate (i.e., the nucleoside-modified substrate) in subsequent iterations; (b) optionally, but preferably, blocking (capping) unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps.

The coupling can be performed by depositing drops of an activator and phosphoramidite at the specific desired feature locations for the array. The activator may be deposited prior to, or after, depositing the phosphoramidite reagent. The functionalized substrate (in the first cycle) or deprotected coupled nucleoside (in subsequent cycles) provides a substrate bound moiety with a linking group for forming the phosphite linkage with a next nucleoside to be coupled in step (a). A number of reagents involved in the above synthetic steps such as, for example, phosphoramidite reagents, are sensitive to moisture and anhydrous conditions and solvents are employed. Final deprotection of nucleoside bases can be accomplished using alkaline conditions in a known manner. For example, one final deprotection step is one in which nitrogenous bases and phosphate group are simultaneously deprotected by treatment with ammonium hydroxide and/or methylamine under known conditions.

Capping, oxidation and deprotection can be accomplished by treating the entire substrate ("flooding") with a layer of the appropriate reagent. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in another flooding procedure in a known manner. Conventionally, a single pulse jet or other dispenser is assigned to deposit a single monomeric unit.

The foregoing chemistry of the synthesis of polynucleotides is described in detail, for example, in Caruthers, *Science* 230: 281-285, 1985; Itakura, et al., *Ann. Rev. Biochem.* 53: 323-356; Hunkapillar, et al., *Nature* 310: 105-110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, and 5,869,643, EP 0294196, and elsewhere.

As mentioned above, various ways may be employed to produce an array of polynucleotides on the surface of a substrate such as a glass substrate. One in situ method employs inkjet printing technology to dispense the appropriate phosphoramidite reagents and other reagents onto individual sites on a surface of a substrate. Oligonucleotides are synthesized on a surface of a substrate in situ using phosphoramidite chemistry. Solutions containing nucleotide monomers and other reagents as necessary such as an activator, e.g., tetrazole, are applied to the surface of a substrate by means of thermal ink-jet technology. Individual droplets of reagents are applied to reactive areas on the surface using, for example, a thermal ink-jet type nozzle. The surface of the substrate may have an alkyl bromide trichlorosilane coating to which is attached polyethylene glycol to provide terminal hydroxyl groups. These hydroxyl groups provide for linking to a terminal primary amine group on a monomeric reagent. Excess of non-reacted chemical on the surface is washed away in a subsequent step. For example, see U.S. Pat. No. 5,700,637 and PCT WO 95/25116 and PCT application WO 89/10977.

Another approach for fabricating an array of biopolymers on a substrate using a biopolymer or biomonomer fluid and using a fluid dispensing head is described in U.S. Pat. No. 6,242,266 (Schleifer, et al.). The head has at least one jet that can dispense droplets onto a surface of a substrate. The jet includes a chamber with an orifice and an ejector, which, when activated, causes a droplet to be ejected from the orifice. Multiple droplets of the biopolymer or biomonomer fluid are dispensed from the head orifice so as to form an array of droplets on the surface of the substrate.

In another embodiment (U.S. Pat. No. 6,232,072) (Fisher) a method of, and apparatus for, fabricating a biopolymer array is disclosed. Droplets of fluid carrying the biopolymer or biomonomer are deposited onto a front side of a transparent substrate. Light is directed through the substrate from the front side, back through a substrate backside and a first set of deposited droplets on the first side to an image sensor.

An example of another method for chemical array fabrication is described in U.S. Pat. No. 6,180,351 (Cattell). The method includes receiving from a remote station information on a layout of the array and an associated first identifier. A local identifier is generated corresponding to the first identifier and associated array. The local identifier is shorter in length than the corresponding first identifier. The addressable array is fabricated on the substrate in accordance with the received layout information.

As mentioned above, a droplet dispensing device employed in embodiments of the present methods normally includes a reagent source, which may be, e.g., a manifold or reservoir or well, and reagent lines that connect the source to fluid dispensing nozzles and the like. Any system may be employed that dispenses fluids such as water, aqueous media, organic solvents and the like as droplets of liquid. The droplet dispensing device may comprises a pump for moving fluid and may also comprise a valve assembly and a manifold as well as a means for delivering predetermined quantities of fluid to the surface of a substrate. The fluids may be dispensed by any of the known techniques. Any standard pumping technique for pumping fluids may be employed in the droplet dispensing device. For example, pumping may be by means of a peristaltic pump, a pressurized fluid bed, a positive displacement pump, e.g., a syringe pump, and the like. The droplet dispensing device may also include suitable valves for assisting in controlling the flow of reagent fluid to designated dispensing nozzles or other elements of the droplet dispensing device.

In another approach reagents for in situ synthesis or DNA can be loaded into a drop dispenser in the form of an inkjet head and fired onto the surface of the support. Such a technique has been described, for example, in PCT publications WO 95/25116 and WO 98/41531, and elsewhere. This method has the advantage of non-contact deposition. Other methods involve pipetting apparatus and positive displacement pumps such as, for example, the Biodot equipment available from Bio-Dot Inc., Irvine Calif., USA.

Other procedures are known in the art for deposition of polynucleotides, particularly DNA such as whole oligomers or cDNA; such procedures are often referred to as direct deposition techniques. One such procedure involves loading a small volume of DNA in solution in one or more drop dispensers such as the tip of a pin or in an open capillary and touching the pin or capillary to the surface of the substrate. Such a procedure is described in U.S. Pat. No. 5,807,522. When the fluid touches the surface, some of the fluid is transferred. The pin or capillary must be washed prior to picking up the next type of DNA for spotting onto the array. This process is repeated for many different sequences and, eventually, the desired array is formed.

In one specific embodiment a droplet dispensing device comprises one or more heads. Each head carries hundreds of ejectors or nozzles to deposit droplets. In the case of heads, each ejector may be in the form of an electrical resistor operating as a heating element under control of a processor (although piezoelectric elements could be used instead). Each orifice with its associated ejector and a reservoir chamber, acts as a corresponding pulse-jet with the orifice acting as a nozzle. In this manner, application of a single electric pulse to an ejector causes a droplet to be dispensed from a corresponding orifice (or larger droplets could be deposited by using multiple pulses to deposit a series of smaller droplets at a given location).

The dispensing head may be of a type commonly used in an ink jet type of printer and may, for example, have one hundred fifty drop dispensing orifices in each of two parallel rows, six chambers for holding solutions of nucleotide precursors communicating with the three hundred orifices, and three hundred ejectors which are positioned in the chambers opposite a corresponding orifice. Thus, there are three hundred pulse jets in this exemplary configuration, although it will be appreciated that a dispensing head could, for example, have more or less pulse jets as desired (for example, at least ten or at least one hundred pulse jets). In this manner, application of a single electric pulse to an ejector causes a droplet to be dispensed from a corresponding orifice. Certain elements of the dispensing head can be adapted from parts of a commercially available thermal inkjet print head device available from Hewlett-Packard Co. as part no. HP51645A. The foregoing dispensing head and other suitable dispensing head designs are described in more detail in U.S. Pat. No. 6,461,812 entitled "A Multiple Reservoir Ink Jet Device for the Fabrication of Biomolecular Arrays," the relevant disclosure of which is incorporated herein by reference.

As is well known in the art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, and so forth. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s (meter/second), usually more than about 10 m/s, and may be as great as about 20 m/s or greater. Droplet dispensing devices include, for example, pulse jets, and so forth.

As mentioned briefly above, the present methods provide for synthesizing a plurality of biopolymers at predetermined feature locations or sites on a surface of a substrate. One or more of the feature locations comprises degenerate biopolymers. One or more biopolymer subunit precursors are added, in multiple rounds of subunit additions, at each of multiple feature locations on the surface to form the plurality of biopolymers on the surface. For each feature location comprising degenerate biopolymers, the biopolymer subunit precursors comprise a mixture of biopolymer subunit precursors for forming the degenerate biopolymers at the feature location.

The mixture of biopolymer subunit precursors at each predetermined feature location may be realized in several different ways. In one approach, additional reservoirs are included in fluid communication with the nozzles or ejectors of a droplet dispensing device. The additional reservoirs contain mixtures of biopolymer subunit precursors in predetermined ratios. The predetermined ratio of the biopolymer subunit precursors is adjusted based upon what is known in the scientific literature about the expected target sequences to be detected and by the expected complexity of the degenerate biopolymers in the sample solution, and so forth. The concentration of the biopolymer subunit precursors is usually equimolar but in certain circumstances may be other than equimolar. Addition of the desired biopolymer subunit mixture at a predetermined feature location is achieved by programming the synthesis apparatus so that the nozzle or ejector in fluid communication with one of the additional reservoirs is activated to deposit the desired mixture at the predetermined feature location. The conditions and other reagents for carrying out the synthesis depend on the nature of the biopolymer subunit precursors and so forth. Generally, such conditions are familiar to those skilled in the art for the particular biopolymers to be synthesized.

The following example is illustrative and is not meant to be a limitation on the scope of the present methods and apparatus. In the 16 mer below there is an expected degeneracy or complexity at position 5 (shown with underlining) so that a feature on an array is synthesized in accordance with the present invention with all four of the possible nucleotide variations in the oligonucleotides that comprise the feature.

```
ACTGCTGATGACGACT        (SEQ ID NO: 1)
ACTGGTGATGACGACT        (SEQ ID NO: 2)
ACTGATGATGACGACT        (SEQ ID NO: 3)
ACTGTTGATGACGACT        (SEQ ID NO: 4)
```

The ratio of oligonucleotides in the mixture parallels the expected ratio of the degenerate polynucleotides in a sample. The synthesis is achieved in accordance with the present invention by dispensing nucleotide precursors at the feature site so that, after the addition of nucleotide precursor corresponding to G at position 4, a mixture of nucleotide precursors corresponding to C, G, A and T is dispensed at position 5 in the next round of additions. To this end an additional reservoir and corresponding nozzle are included in the dispensing system. The additional reservoir contains all four of the above nucleotide precursors in a predetermined ratio, which is dispensed to the feature site using the additional nozzle. Alternatively, existing reservoirs each containing one of the four nucleotide precursors may be employed to dispense predetermined amounts of the nucleotide precursors to the feature site to form the mixture. In this latter approach activator should be added subsequent to depositing the complete mixture of nucleotide precursors.

Another example, by way of illustration and not limitation, is discussed below where the oligonucleotides have degeneracy at positions 5 and 6 (shown with underlining) resulting in a 16-fold increase in complexity of sequences per feature. A feature on an array is synthesized in accordance with the present invention with all sixteen of the possible nucleotide variations at positions 5 and 6 in the mixture of oligonucleotides that comprise the feature.

```
ACTGCTGATGACGACT          (SEQ ID NO: 5)
ACTGCGGATGACGACT          (SEQ ID NO: 6)
ACTGCCGATGACGACT          (SEQ ID NO: 7)
ACTGCAGATGACGACT          (SEQ ID NO: 8)
ACTGGTGATGACGACT          (SEQ ID NO: 9)
ACTGGGGATGACGACT          (SEQ ID NO: 10)
ACTGGCGATGACGACT          (SEQ ID NO: 11)
ACTGGAGATGACGACT          (SEQ ID NO: 12)
ACTGATGATGACGACT          (SEQ ID NO: 13)
ACTGAGGATGACGACT          (SEQ ID NO: 14)
ACTGACGATGACGACT          (SEQ ID NO: 15)
ACTGAAGATGACGACT          (SEQ ID NO: 16)
ACTGTTGATGACGACT          (SEQ ID NO: 17)
ACTGTGGATGACGACT          (SEQ ID NO: 18)
ACTGTCGATGACGACT          (SEQ ID NO: 19)
ACTGTAGATGACGACT          (SEQ ID NO: 20)
```

The ratio of oligonucleotides in the mixture parallels the expected ratio of the degenerate polynucleotides in a sample. The synthesis is achieved in accordance with the present invention by first dispensing nucleotide precursors at the feature site so that, after the addition of nucleotide precursor corresponding to G at position 4, a mixture of nucleotide precursors corresponding to C, G, A and T is dispensed at position 5 in the next round of additions. This may be accomplished as described above. In the next round of additions synthesis is achieved in accordance with the present invention by dispensing nucleotide precursors at the feature site so that, after the addition of nucleotide precursor corresponding to C, G, A or T at position 5, a mixture of nucleotide precursors corresponding to C, G, A and T is dispensed at position 6 in the next round of additions. Again, this may be accomplished as described above.

The general case of substituting base combinations for a single base is most easily expressed using standard nucleotide "wobble codes," which means that letters are assigned to represent equimolar mixtures of bases at given sequence positions. It should be noted that in the present invention the mixtures of oligonucleotides at a feature site may be equimolar but need not be as explained hereinabove.

| Single Base Codes | Combinations of 2 Bases | Combinations of 3 Bases | Combinations of 4 Bases |
|---|---|---|---|
| A | A + C = M | A + C + G = V | A + T + G + C = N |
| T | A + G = R | A + C + T = H | |
| G | A + T = W | A + G + T = D | |
| C | C + G = S | C + G + T = B | |
|   | C + T = Y | | |
|   | G + T = K | | |

Thus, for example, oligonucleotides SEQ ID NOS: 1-4 given above, namely,

```
ACTGCTGATGACGACT          (SEQ ID NO: 1)
ACTGGTGATGACGACT          (SEQ ID NO: 2)
ACTGATGATGACGACT          (SEQ ID NO: 3)
ACTGTTGATGACGACT          (SEQ ID NO: 4)
``` may be written as:
   ACTGNTGATGACGACT (SEQ ID NO: 21)

which is shorthand for an equimolar combination of oligonucleotides SEQ ID NOS: 1-4, above. The signal measured by this probe is the average of the signals that would be measured by the 4 individual probes that have been combined into one probe feature.

This approach can be generalized to variations at more than one position. For instance, oligonucleotides SEQ ID NOS: 5-20 above may be rewritten as:
   ACTGNNGATGACGACT (SEQ ID NO: 22)

which is shorthand for an equimolar combination of oligonucleotides SEQ ID NOS:5-20 all in one probe location or feature site. The signal measured by probe SEQ ID NOS:22 is the average of the signals that would be measured by the 12 individual probes that have been combined into one probe feature.

Such an array comprising the aforementioned feature sites may be manufactured by printing phosphoramidites by, for example, adding up to four extra printing heads (one for up to each possible mixture of four bases or nucleotide precursors). This is much less expensive than the addition of an entire extra masking step that would be required if the array were synthesized via photolithography. If array synthesis is performed by either in situ phosphoramidite chemistry or conventional phosphoramidite chemistry followed by deposition and linkage of whole oligonucleotides to the surface, then such a combination probe can easily be synthesized by using a mixture of phosphoramidites to perform the synthetic step at the desired position.

As mentioned above another embodiment of the present invention is an apparatus for synthesizing an array of biopolymers on a surface of a substrate. The apparatus comprises a dispensing device comprising a plurality of nozzle groups. Each of the nozzle groups is in fluid communication with a reservoir wherein at least one of the reservoirs contains a mixture of biopolymer subunit precursors.

Figure 4:
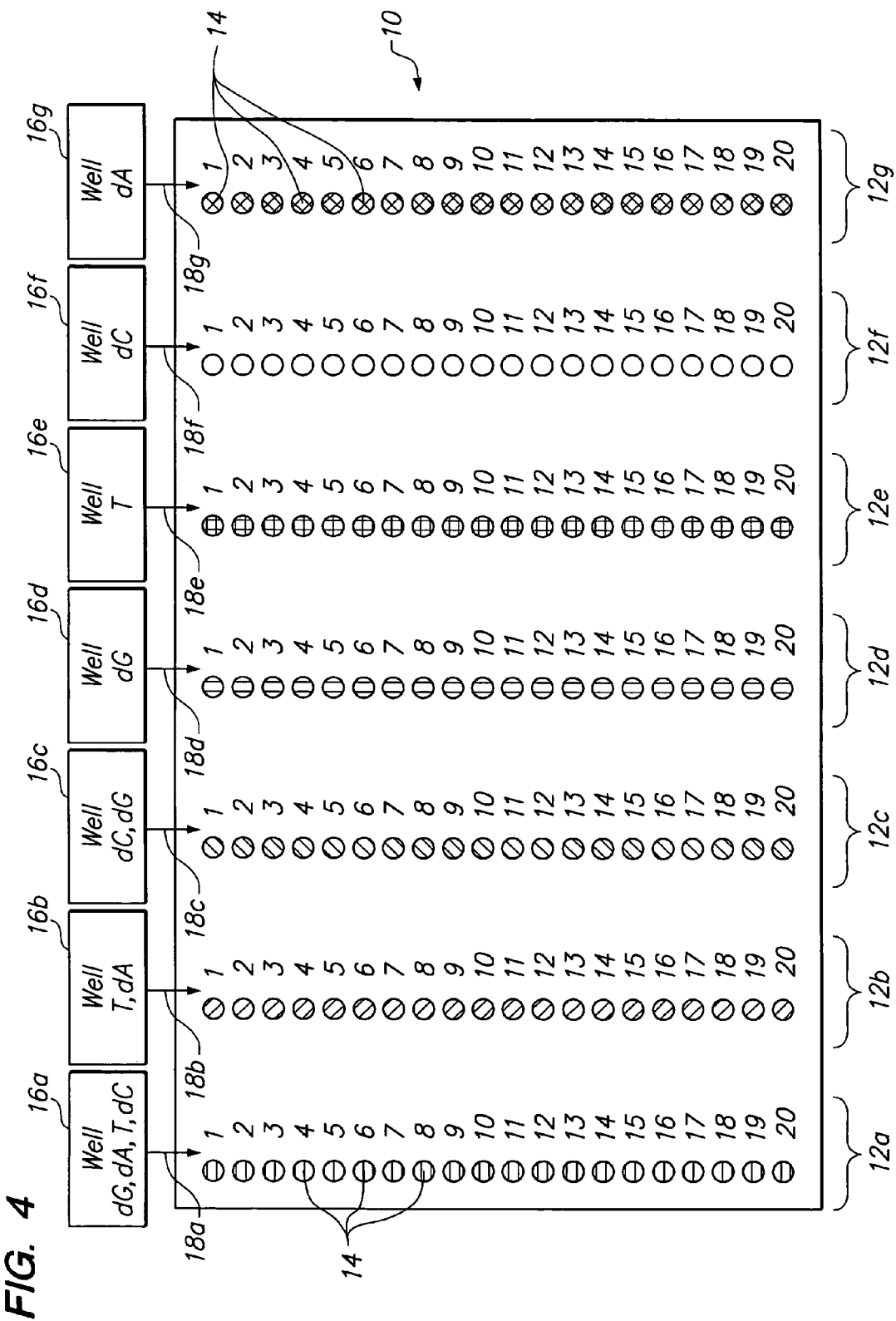
FIG. 4 is a schematic diagram of a dispensing head containing groups of 20 nozzles, which may be used in accordance with the present invention.

A dispensing head that may be employed in the present invention is illustrated in FIG. 4 by way of example and not limitation. Dispensing head 10 comprises seven groups 12a-12g of nozzles 14, each group having twenty nozzles. It should be noted that, although twenty nozzles are shown per group, a dispensing head may comprise any number of nozzle groups such as, e.g., about 1, about 2, about 3, about 4, about 5, about 10, about 20, about 30, about 40, about 50, about 100 up to about 1,000, about 2,000, about 3,000, about 4,000, about 5,000, about 10,000, about 20,000, about 30,000, about 40,000, about 50,000, about 100,000 or more and so forth. Each nozzle group is in fluid communication with a respective well 16a-16g by means of fluid lines 18a-18g, which may be any suitable conduit for fluid flow. Each well contains a different one or set of nucleotide precursors. In the example shown in FIG. 4, well 16a contains nucleotide precursors dG, dA, T and dC. Well 16b contains nucleotide precursors T and dA; well 16c contains nucleotide precursors dC and dG. Wells 16d-16g contain respectively dG, T, dC or dA.

Figure 5:
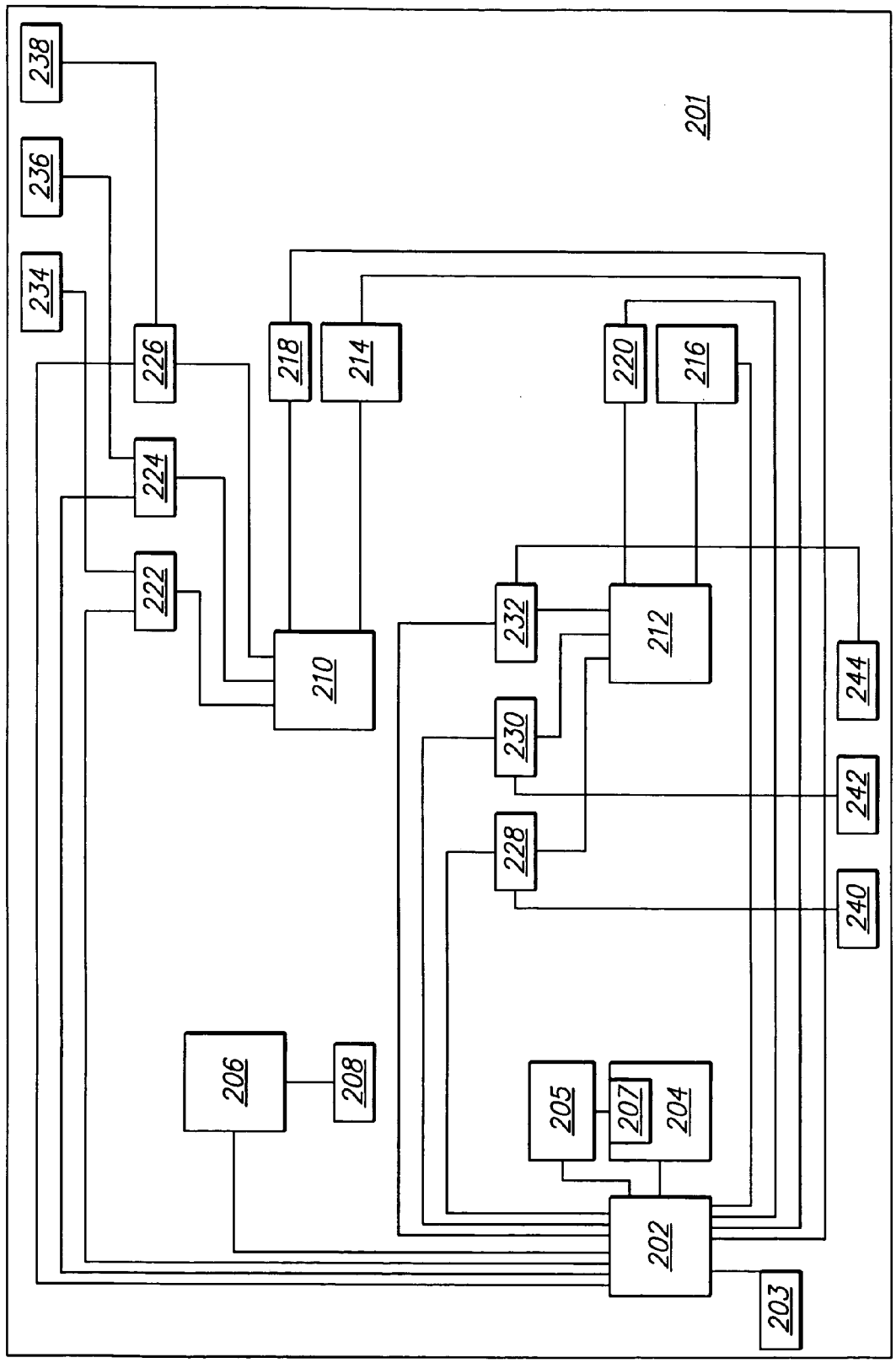
FIG. 5 is a schematic diagram of an apparatus for synthesizing an array of biopolymers on a surface of a substrate where the apparatus includes a dispensing head in accordance with the present invention.
Figure 6:
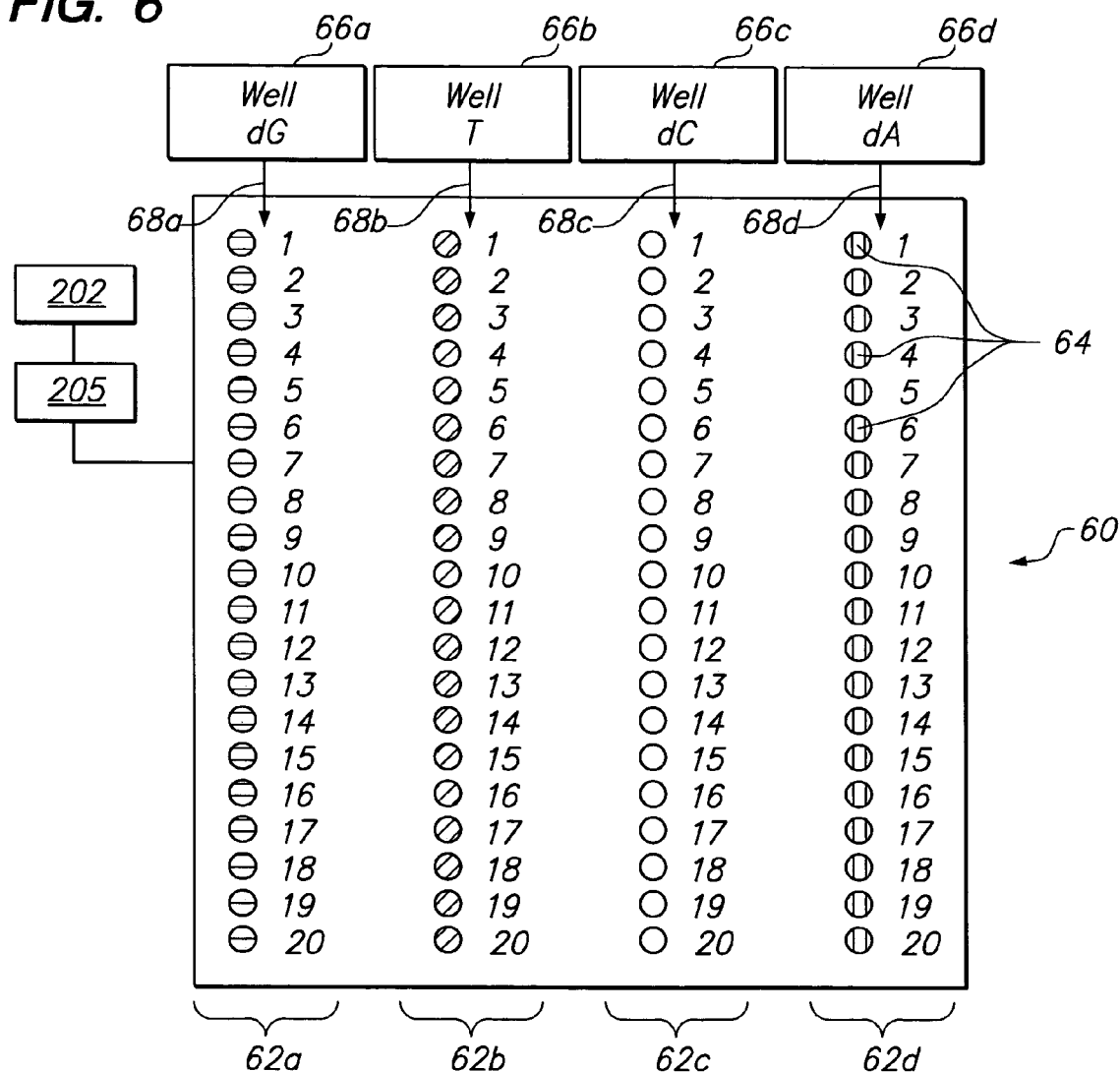
FIG. 6 is a schematic diagram of another embodiment of a dispensing head containing groups of 20 nozzles, which may be used in accordance with the present invention.

One embodiment of an apparatus that includes a dispensing device in accordance with the present invention is depicted in FIG. 5 in schematic form. Apparatus 200 comprises platform 201 on which the components of the apparatus are mounted. Apparatus 200 comprises main computer 202, with which various components of the apparatus are in communication. Video display 203 is in communication with computer 202. Apparatus 200 further comprises reaction chamber 204, which is controlled by main computer 202. The nature of reaction chamber 204 depends on the nature of the deposition technique employed to add monomers to a growing polymer chain. Such deposition techniques include, by way of illustration and not limitation, pulse-jet deposition, and so forth as discussed above. Reaction chamber 204 comprises droplet dispensing device 10 (FIG. 4) or droplet dispensing device 60 (FIG. 6). Mechanism 205 is controlled by main computer 202 and moves a droplet dispensing device 207 in reaction chamber 204 into position for depositing, cleaning, priming and so forth. Transfer robot 206 is also controlled by main computer 202 and comprises a robot arm 208 that moves a support to and from reaction chamber 204. The support may be moved to one or more flow cells such as first flow cell 210 or second flow cell 212 for carrying out various procedures for synthesizing the biopolymers such as, for example, oxidation steps, blocking or deblocking steps and so forth. First flow cell 210 is in communication with program logic controller 214, which is controlled by main computer 202, and second flow cell 212 is in communication with program logic controller 216, which is also controlled by main computer 202. First flow cell 210 is in communication with flow sensor and level indicator 218, which is controlled by main computer 202, and second flow cell 212 is in communication with flow sensor and level indicator 220, which is also controlled by main computer 202. First flow cell 210 is in fluid communication with manifolds 222, 224 and 226, each of which is controlled by main computer 202 and each of which is in fluid communication with a source of fluid reagents, namely, 234, 236 and 238, respectively. Second flow cell 212 is in fluid communication with manifolds 228, 230 and 232, each of which is controlled by main computer 202 and each of which is in fluid communication with a source of fluid reagents, namely, 240, 242 and 244, respectively.

The components of the apparatus are normally mounted on a suitable frame in a manner consistent with the present invention. The frame of the apparatus is generally constructed from a suitable material that gives structural strength to the apparatus so that various moving parts may be employed in conjunction with the apparatus. Such materials for the frame include, for example, metal, lightweight composites, granite and the like.

The apparatus may also comprise a loading station for loading reagents into the dispensing device and a mechanism for moving the dispensing device and/or the loading station relative to one another. The apparatus may also comprise a wash station for washing the dispensing device and a mechanism for moving the dispensing device and/or the wash station relative to one another. The apparatus further may comprise a mechanism for inspecting the reagent deposited on the surface of the substrate.

The substrate mount may be any convenient structure on which the substrate may be placed and held for depositing reagents on the surface of the substrate. The substrate mount may be of any size and shape and generally has a shape similar to that of the substrate as long as it is sufficiently able to support the substrate. For example, the substrate mount is rectangular for a rectangular substrate, circular for a circular substrate and so forth. The substrate mount may be constructed from any material of sufficient strength to physically receive and hold the substrate during the deposition of reagents on the substrate surface as well as to withstand the rigors of movement in one or more directions. Such materials include metal, composites, and the like. The support or substrate may be retained on the substrate mount by gravity, friction, vacuum, and the like. The surface of the substrate mount, on which the substrate is received, may be flat or may comprise certain structural features such as, for example, parallel upstanding linear ribs, and the like, on which the substrate is placed.

Another embodiment of an apparatus for synthesizing an array of biopolymers on a surface of a substrate comprises a dispensing device comprising a plurality of nozzle groups. Each of the nozzle groups is in fluid communication with a reservoir. Each of the reservoirs contains a fluid comprising a single biopolymer subunit precursor. The apparatus further comprises a control unit that activates the dispensing device to dispense one or more drops of fluid comprising the biopolymer subunit precursor at individual feature sites on the surface to deposit a single biopolymer subunit precursor at an individual feature site or to deposit two or more biopolymer subunit precursors at an individual feature site to form a mixture of biopolymer subunit precursors at the individual feature site.

An example of a dispensing head discussed above that may be employed in the present invention is illustrated in FIG. 6 by way of example and not limitation. Dispensing head 60 comprises four groups 62a-62d of nozzles 64, each group having twenty nozzles. It should be noted that, although twenty nozzles are shown per group, a dispensing head may comprise any number of nozzle groups as discussed above for dispensing head 10. Each nozzle group is in fluid communication with a respective well 66a-66d by means of fluid lines 68a-68d, which may be any suitable conduit for fluid flow. Each well contains a different nucleotide precursor. In the example shown in FIG. 6, wells 16a-16d contain respectively dG, T, dC or dA. The dispensing head 60 further comprises computer 202 (as discussed above for FIG. 5), which serves as a control unit. One function of the computer is to activate the dispensing device to dispense one or more drops of fluid comprising the biopolymer subunit precursor at individual feature sites on the surface of a substrate. The dispensing device may be activated to deposit a single biopolymer subunit precursor at an individual feature site or to deposit two or more biopolymer subunit precursors at an individual feature site to form a mixture of biopolymer subunit precursors at the individual feature site.

Any suitable computer may be employed in the present methods and apparatus. For example, an IBM® compatible personal computer (PC) may be utilized. The computer is driven by software specific to the methods described herein.

The preferred computer hardware capable of assisting in the operation of the methods in accordance with the present invention involves a system with at least the following specifications: Pentium® processor or better with a clock speed of at least 100 MHz, at least 32 megabytes of random access memory (RAM) and at least 80 megabytes of virtual memory, running under either the Windows 95 or Windows NT 4.0 operating system (or successor thereof).

As mentioned above, software that may be used to carry out the methods may be, for example, Microsoft Excel or Microsoft Access, suitably extended via user-written functions and templates, and linked when necessary to standalone programs that calculate specific parameters (e.g., MFOLD for intramolecular thermodynamic parameters). Examples of software programs used in assisting in conducting the present methods may be written, preferably, in Visual BASIC, FORTRAN and C++, as exemplified below in the Examples. It should be understood that the above computer information and the software used herein are by way of example and not limitation. The present methods may be adapted to other computers and software. Other languages that may be used include, for example, PASCAL, PERL or assembly language.

As mentioned above, the methods and reagents of the present invention are particularly useful in the area of oligonucleotide arrays. One aspect of the present invention is an addressable array comprising a support having a surface, a spot on the surface having bound thereto an oligonucleotide probe specific for a target nucleic acid sequence and at least one spot on the surface having bound thereto a mixture of oligonucleotide probes which differ by having one or more sites of degeneracy. The probes are employed in an effective amount, namely, an amount that will yield the desired result such as detection of a target nucleic acid sequence and/or the differentiation of, and determination of the amounts of, respective degenerate polynucleotides in a target sample. Different signal producing systems may be employed for each suspected degenerate polynucleotide to be detected.

A method for detecting a target nucleic acid sequence(s) comprises contacting a medium suspected of containing the target nucleic acid sequence(s) with the above addressable array and determining a result of the contacting. The result indicates the presence or absence of the target nucleic acid sequence in the medium and/or the presence and amounts of degenerate target nucleic acids. The result may be determined by examining the array for the presence of a hybrid of a target nucleic acid sequence and the oligonucleotide probe specific for the target nucleic acid sequence. The presence of the hybrid indicates the presence of the target nucleic acid sequence(s) in the medium. In one approach the target nucleic acid sequence is labeled and the result is determined by examining the array for the presence of signal associated with the label, the signal being related to the presence of the hybrid. Different signal producing systems may be employed for each suspected degenerate polynucleotide to be detected.

Reading of the array may be accomplished by illuminating the array and reading the location and intensity of resulting fluorescence at each feature of the array. For example, a scanner may be used for this purpose where the scanner may be similar to, for example, the AGILENT MICROARRAY SCANNER available from Agilent Technologies Inc, Palo Alto, Calif. Other suitable apparatus and methods are described in U.S. patent application Ser. No. 09/846,125 "Reading Multi-Featured Arrays" by Dorsel, et al.; and U.S. Pat. No. 6,406,849. The relevant portions of these references are incorporated herein by reference. However, arrays may be read by methods or apparatus other than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. Nos. 6,221,583 and 6,251,685, and elsewhere). In addition, an apparatus according to FIG. 3 may be employed to scan the linear arrays.

Results from the reading may be raw results (such as fluorescence intensity readings for each feature in one or more color channels) or may be processed results such as obtained by rejecting a reading for a feature that is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

One aspect of the invention is the product of the above method, namely, the assay result, which may be evaluated at the site of the testing or it may be forwarded to a remote location, e.g., another site, for evaluation and communication to an interested party.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

As mentioned above, the methods of the present invention are preferably carried out at least in part with the aid of a computer. The considerations regarding the computer, computer software, and the like are similar or the same as those discussed above. A computer program may be utilized to carry out the above method steps. The computer program provides for adding one or more biopolymer subunit precursors, in multiple rounds of subunit additions, at each of multiple feature locations on the surface of a substrate to form the plurality of biopolymers on the surface. For each feature location comprising degenerate biopolymers, the biopolymer subunit precursors comprise a mixture of biopolymer subunit precursors for forming the degenerate biopolymers at the feature location.

Another aspect of the present invention is a computer program product comprising a computer readable storage medium having a computer program stored thereon which, when loaded into a computer, selects the appropriate series of steps to carry out a synthesis of biopolymers on the surface of a substrate in accordance with the present invention. The computer program provides for the performance of steps as discussed above.

As indicated above, any of the steps of the methods of the present invention can be executed on a suitable computer system. The computer system may be programmed from a computer readable storage medium that carries code for the system to execute the steps required of it. The computer readable storage medium may comprise, for example, magnetic storage media such as optical disc, optical tape, or machine readable bar code, solid state electronic storage devices such as random access memory (RAM), or read only memory (ROM), or any other physical device or medium that might be employed to store a computer program. It will also be understood that computer systems of the present invention can include the foregoing programmable systems and/or hardware or hardware/software combinations that can execute the same or equivalent steps.

As mentioned briefly above, arrays synthesized in accordance with the invention may be used for normalization for nucleic acid microarrays. Normalization is a general problem in the analysis of data from nucleic acid microarrays hybridized to samples labeled in two or more colors. Normalization is the process by which the data from all color channels is brought onto the same relative scale. Such rescaling is a prerequisite to the calculation of differential expression ratios; if the data are not on the same relative scale, then the expression ratios calculated from the data will be multiplied by some unknown factor or function.

Current methods of normalization rely on two steps. Step 1 comprises identification of a subset of the data for which the expression ratio (at least, on average) is believed to be known. Examples include the use of a set of housekeeping genes, i.e., genes believed to be uniformly expressed in different sample types) or the use of all statistically significant data (if the number of differentially expressed genes is believed to be small compared to the total population). Step 2 comprises resealing of both data channels according to some model. The model may be as simple as division of all data in each channel by the arithmetic or geometric mean of the data in that channel or as complex as fitting to a non-linear function.

Embodiments of the present invention provide a separate means of normalizing data for multiple arrays based on the hybridization intensities (in one or more color channels) of each array to a set of degenerate oligonucleotide probes. An additional result of this method is a measure of the degeneracy inherent to each sample being tested.

Embodiments of the present invention provide for normalizing results of binding reactions such as hybridization reactions between, for example, polynucleotides and oligonucleotide probes. A plurality of samples suspected of containing target molecules such as, for example, samples from different individuals and the like are analyzed using a plurality of arrays. Each array comprises features on a surface of a substrate. A respective array from the plurality of arrays is contacted with a respective sample from the plurality of samples under conditions for binding to occur between target molecules in the sample and biopolymers on the surface. Such conditions include time, temperature, pH, and so forth and are generally known to those skilled in the art. For example, hybridization conditions, e.g., stringent hybridization conditions, are employed where the target molecules are polynucleotides. Each of the arrays comprises a plurality of biopolymers at predetermined feature locations on the surface. One or more of the feature locations on each of the arrays comprise molecules of the same degenerate biopolymers. In other words, each of the arrays comprises the same degenerate biopolymers. The arrays are examined for the results of the binding reactions by, for example, examination methods discussed above. The results of the binding reactions involving the degenerate biopolymers are used to normalize the results of the binding reactions across all of the arrays.

Kits of the Invention

Another aspect of the present invention relates to kits useful for conveniently performing a method in accordance with the invention. To enhance the versatility of the subject invention, the reagents can be provided in packaged combination, in the same or separate containers, so that the ratio of the reagents provides for substantial optimization of the method. The reagents may each be in separate containers or various reagents can be combined in one or more containers depending on the cross-reactivity and stability of the reagents.

In one embodiment a kit comprises an addressable array described above. The kit can further include other separately packaged reagents for conducting an analysis method such as hybridization reactions using the addressable array as well as ancillary reagents and so forth. The relative amounts of the various reagents in the kits can be varied widely to provide for concentrations of the reagents that substantially optimize the reactions that need to occur during the present method. Under appropriate circumstances one or more of the reagents in the kit can be provided as a dry powder, usually lyophilized, including excipients, which on dissolution will provide for a reagent solution having the appropriate concentrations for performing a method in accordance with the present invention. The kit can further include a written description of a method in accordance with the present invention as described above.

The reagents, methods and kits of the invention are useful for, among others, mutation detection, mutation identification, polymorphism analysis, genotyping, de novo sequencing, re-sequencing, gene expression profiling, cDNA clustering and the like.

It should be understood that the above description is intended to illustrate and not limit the scope of the invention. Other aspects, advantages and modifications within the scope of the invention will be apparent to those skilled in the art to which the invention pertains. The invention has application to biopolymers in general such as, for example, polynucleotides, poly (amino acids), e.g., proteins and peptides, and the like.

All publications and patent applications cited in this specification are herein incorporated by reference as if each individual publication or patent application where specifically and individually indicated to be incorporated by reference.

Although embodiments of the foregoing invention have been described in some detail by way of illustration and example for purposes of clarity of understanding, it will be readily apparent to those of ordinary skill in the art in light of the teachings of this invention that changes and modifications may be made thereto without departing from the spirit or scope of the appended claims. Furthermore, the foregoing description, for purposes of explanation, used specific nomenclature to provide a thorough understanding of the invention. However, it will be appreciated that one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for synthesizing a plurality of biopolymers comprising nucleotides at predetermined feature locations on a surface of a substrate wherein a feature location of said feature locations comprises degenerate biopolymers comprising nucleotides, said method comprising:
producing a mixture of two or more different biopolymer subunit precursors; and
providing said mixture to a predetermined feature location on said surface of said substrate in a round of multiple rounds of subunit additions to produce the feature location comprising degenerate biopolymers.

2. A method according to claim 1 wherein said biopolymers are polynucleotides.

3. A method according to claim 1 wherein said degenerate biopolymers comprise a contiguous stretch of 1 to 5 degenerate nucleotides.

4. The method of claim 1, wherein said biopolymer subunit precursors are nucleotide precursors.

5. The method of claim 4, wherein said mixture of different biopolymer subunit precursors comprises nucleotide precursors corresponding to C, G, A and T.

6. The method of claim 1, wherein said biopolymer subunit precursors are monomers.

7. The method of claim 1, wherein said degenerate biopolymer feature location comprises degenerate biopolymers having less than 10 sites of degeneracy.

8. A method for synthesizing a plurality of biopolymers comprising nucleotides at predetermined feature locations on a surface of a substrate wherein a feature location of said feature locations comprises degenerate biopolymers comprising nucleotides, said method comprising, in each round of multiple rounds of subunit additions, providing biopolymer subunit precursors at each of multiple feature locations on said surface to form said plurality of said biopolymers on said surface, wherein, for the feature location comprising said degenerate biopolymers, said biopolymer subunit precursors for a round of said multiple rounds are provided as a mixture of two or more different biopolymer subunit precursors for forming said degenerate biopolymers, each round of subunit additions comprising
- (a) dispensing from a dispensing system said biopolymer subunit precursors to said predetermined feature locations,
- (b) dispensing activator to said predetermined feature locations, and
- (c) repeating steps (a)-(b).

9. A method according to claim 8 wherein said biopolymers are polynucleotides.

10. A method according to claim 8 wherein said degenerate biopolymers comprise a contiguous stretch of 1 to 5 degenerate nucleotides.

11. A method according to claim 8 wherein said biopolymers are oligonucleotides.

12. A method according to claim 8 wherein said dispensing system comprises at least one droplet dispensing device.

13. The method of claim 12, wherein said droplet dispensing device comprises a reservoir comprising said mixture.

14. A method according to claim 8, which is a computer based method wherein steps (a) through (c) are carried out under computer control.

15. The method of claim 8, wherein said biopolymer subunit precursors are nucleotide precursors.

16. The method of claim 15, wherein said mixture of different biopolymer subunit precursors comprises nucleotide precursors corresponding to C, G, A and T.

17. The method of claim 8, wherein said biopolymer subunit precursors are monomers.

18. A method for synthesizing a plurality of biopolymers comprising nucleotides at predetermined feature locations on a surface of a substrate, wherein a feature location of said feature locations comprises degenerate biopolymers comprising nucleotides, said method comprising, in each round of multiple rounds of subunit additions, providing biopolymer subunit precursors at each of multiple feature locations on said surface to form said plurality of said biopolymers on said surface, wherein, for the feature location comprising said degenerate biopolymers, said biopolymer subunit precursors for a round of said multiple rounds are provided as a mixture comprising a predetermined ratio of two or more different biopolymer subunit precursors for forming said degenerate biopolymers, each round of subunit additions comprising
- (a) dispensing from a dispensing system said biopolymer subunit precursors to said predetermined feature locations in a droplet manner,
- (b) dispensing activator to said predetermined feature locations, and
- (c) repeating steps (a)-(b) to form said plurality of biopolymers comprising nucleotides at predetermined feature locations on said surface.

19. A method according to claim 18 wherein said biopolymers are polynucleotides.

20. A method according to claim 18 wherein said degenerate biopolymers comprise a contiguous stretch of 1 to 5 degenerate nucleotides.

21. A method according to claim 18 wherein said biopolymers are oligonucleotides.

22. A method according to claim 18 wherein said dispensing system comprises at least one droplet dispensing device.

23. The method of claim 22, wherein said droplet dispensing device comprises a reservoir comprising said mixture.

24. A method according to claim 18, which is a computer based method wherein steps (a) through (c) are carried out under computer control.

25. The method of claim 18, wherein said biopolymer subunit precursors are nucleotide precursors.

26. The method of claim 25, wherein said mixture comprising a predetermined ratio of different biopolymer subunit precursors comprises nucleotide precursors corresponding to C, G, A and T.

27. The method of claim 18, wherein said biopolymer subunit precursors are monomers.

28. A method for synthesizing a plurality of biopolymers comprising nucleotides at predetermined feature locations on a surface of a substrate, wherein a feature location of said feature locations comprises degenerate biopolymers comprising nucleotides, said method comprising, in each round of multiple rounds of subunit additions, providing biopolymer subunit precursors at each of multiple feature locations on said surface to form said plurality of said biopolymers on said surface, wherein, for the feature location comprising said degenerate biopolymers, said biopolymer subunit precursors for a round of said multiple rounds are provided as a mixture of two or more different biopolymer subunit precursors for forming said degenerate biopolymers.

* * * * *

SEQUENCE LISTING

<160> NUMBER OF SEQ ID NOS: 22

<210> SEQ ID NO 1
<211> LENGTH: 16
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
actgctgatg acgact                                                        16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
actggtgatg acgact                                                        16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
actgatgatg acgact                                                        16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actgttgatg acgact                                                        16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
actgctgatg acgact                                                        16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
actgcggatg acgact                                                        16

<210> SEQ ID NO 7
<211> LENGTH: 16
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 7
actgccgatg acgact                                                         16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
actgcagatg acgact                                                         16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
actggtgatg acgact                                                         16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
actggggatg acgact                                                         16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
actggcgatg acgact                                                         16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
actggagatg acgact                                                         16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic

```
                    oligonucleotide

<400> SEQUENCE: 13
actgatgatg acgact                                                    16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
actgaggatg acgact                                                    16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actgacgatg acgact                                                    16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
actgaagatg acgact                                                    16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
actgttgatg acgact                                                    16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
actgtggatg acgact                                                    16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 19
actgtcgatg acgact                                                      16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
actgtagatg acgact                                                      16

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (5)
<223> OTHER INFORMATION: a, t, c or g

<400> SEQUENCE: 21
actgntgatg acgact                                                      16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (5)..(6)
<223> OTHER INFORMATION: a, t, c or g

<400> SEQUENCE: 22
actgnngatg acgact                                                      16
```